United States Patent
Gimble et al.

(10) Patent No.: US 9,512,405 B2
(45) Date of Patent: Dec. 6, 2016

(54) NON-ENZYMATIC METHOD FOR ISOLATING HUMAN ADIPOSE-DERIVED STROMAL STEM CELLS

(71) Applicants: Jeffrey M. Gimble, New Orleans, LA (US); Forum S. Shah, Baton Rouge, LA (US); Xiying Wu, New Orleans, LA (US)

(72) Inventors: Jeffrey M. Gimble, New Orleans, LA (US); Forum S. Shah, Baton Rouge, LA (US); Xiying Wu, New Orleans, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 246 days.

(21) Appl. No.: 13/713,784

(22) Filed: Dec. 13, 2012

(65) Prior Publication Data

US 2014/0017783 A1 Jan. 16, 2014

Related U.S. Application Data

(60) Provisional application No. 61/570,495, filed on Dec. 14, 2011.

(51) Int. Cl.
*C12N 5/06* (2006.01)
*C12N 5/0775* (2010.01)
*A61K 35/35* (2015.01)

(52) U.S. Cl.
CPC ............. *C12N 5/0667* (2013.01); *A61K 35/35* (2013.01)

(58) Field of Classification Search
None
See application file for complete search history.

(56) References Cited

U.S. PATENT DOCUMENTS

| | | | |
|---|---|---|---|
| 6,777,231 B1 | 8/2004 | Katz et al. | 435/325 |
| 7,390,484 B2 | 6/2008 | Fraser et al. | 424/93.7 |
| 7,470,537 B2 | 12/2008 | Hedrick et al. | 435/325 |
| 8,119,121 B2 | 2/2012 | Fraser et al. | 424/93.7 |
| 8,119,398 B2 | 2/2012 | Sayre et al. | 435/325 |
| 8,226,947 B2 | 7/2012 | Presta | 424/131.1 |
| 2013/0034524 A1* | 2/2013 | Agha-Mohammadi | C12N 5/0667 424/93.7 |
| 2013/0115697 A1* | 5/2013 | Alt | C12M 45/05 435/379 |

FOREIGN PATENT DOCUMENTS

WO WO 01/62901 8/2001

OTHER PUBLICATIONS

Yoshimura et al. (Journal of Cellular Physiology, vol. 208, p. 64-76, 2006).*
Francis "Isolating adipose-derived mesenchymal stem cells from lipoaspirate blood and saline fraction" Organogenesis, 2009, 6:1, 11-14.*
Carvalho, P.P. et al., "Use of animal protein-free products for passaging adherent human adipose-derived stromal/stem cells," Cytotherapy, vol. 13, No. 5, pp. 594-597 (2011).
Gimble, J. et al., "Adipose-derived adult stem cells: isolation, characterization, and differentiation potential," Cytotherapy, vol. 5, No. 5, pp. 362-369 (2003).
Gimble, J.M. et al., "Adipose tissue as a stem cell source for musculoskeletal regeneration," Front Biosci (Schol Ed), vol. 3, pp. 69-81 (2011).
Gimble, J.M. et al., "Clinical and preclinical translation of cell-based therapies using adipose tissue-derived cells," Stem Cell Res Ther., 1:19, pp. 1-8 (2010).
Gimble, J.M. et al., "Adipose-derived stem cells for regenerative medicine," Circ Res., vol. 100, pp. 1249-1260 (2007).
Griesche, N. et al., "A simple modification of the separation method reduces heterogeneity of adipose-derived stem cells," Cells Tissues Organs., vol. 192, pp. 106-115 (2010).
Hicok, K.C. et al., "Automated isolation and processing of adipose-derived stem and regenerative cells," Methods Mol Biol., vol. 702, pp. 87-105 (2011).
"Human Cells, Tissues, and Cellular and Tissue-Based Products," Code of Federal Regulations, Title 21, vol. 8 (21CFR1271.3) (2011, revised 2014).
Jurgens, W.J.E.M. et al., "Freshly isolated stromal cells from the infrapatellar fat pad are suitable for a one-step surgical procedure to regenerate cartilage tissue," Cytotherapy, vol. 11, No. 8, pp. 1052-1064 (2009).

(Continued)

*Primary Examiner* — Robert Yamasaki
*Assistant Examiner* — Charles Zoltan Constantine
(74) *Attorney, Agent, or Firm* — Bonnie J. Davis; John H. Runnels

(57) ABSTRACT

A simple method was developed to extract adipose-derived stromal stem cells (ASCs) without using enzymatic digestion of the collagen in adipose tissue. The resulting ASCs isolated by the simple wash method have lower levels of CD34 expression, a hematopoietic stem cell marker, as compared to ASCs isolated using conventional enzymatic digestion using collagenase. This characteristic is consistent with non-enzymatically treated stem cells obtained from bone marrow aspirates, which are negative for CD34. Additionally, the washed ASCs have higher levels of CD44 expression, a hyaluronate receptor, and lower levels of contaminating hematopoietic cells, as evidenced by low CD45 expression, as compared to enzymatically digested cells. The cells produced by this simple method can be used therapeutically for allogenic or autologous tissue regeneration, and can be administered using any pharmaceutically acceptable carrier. In addition, the cells can be administered in a matrix, lattice, scaffold, or other biologically compatible materials.

6 Claims, 4 Drawing Sheets

(56) References Cited

OTHER PUBLICATIONS

Oedayrajsingh-Varma, M.J. et al., "Adipose tissue-derived mesenchymal stem cell yield and growth characteristics are affected by the tissue-harvesting procedure," Cytotherapy, vol. 8, No. 2, pp. 166-177 (2006).

Rada, T. et al., "A novel method for the isolation of subpopulations of rat adipose stem cells with different proliferation and osteogenic differentiation potentials," J Tissue Eng Regen Med., vol. 5, pp. 655-664 (2011).

Rodbell, M., "Metabolism of Isolated Fat Cells. I. Effects of Hormones on Glucose Metabolism and Lipolysis," J Biol Chem., vol. 239, pp. 375-380 (1964).

Shah, F.S., "A Non-Enzymatic Method for Isolating Human Adipose-Derived Stromal Stem Cells," an abstract and poster presented at the 2nd Midwest Conference on Stem Cell Biology and Therapy, Oakland University, Rochester, MI (Oct. 5-7, 2012).

Shah, F.S. et al., "A Non-Enzymatic Method for Isolating Human Adipose-Derived Stromal Stem Cells," a manuscript submitted to Cytotherapy (Nov. 2012).

Williams, S.K. et al., "Collagenase lot selection and purification for adipose tissue digestion," Cell Transplant., vol. 4, iss. 3, pp. 281-289 (1995).

Yoshimura, K. et al., "Characterization of freshly isolated and cultured cells derived from the fatty and fluid portions of liposuction aspirates," J Cell Physiol., vol. 208, pp. 64-76 (2006).

Yu, G. et al., "Yield and characterization of subcutaneous human adipose-derived stem cells by flow cytometric and adipogenic mRNA analyzes," Cytotherapy, vol. 12, pp. 538-546 (2010).

Zuk, P.A. et al., "Human adipose tissue is a source of multipotent stem cells," Mol Biol Cell, vol. 13, pp. 4279-4295 (2002).

Zuk, P.A. et al., "Multilineage cells from human adipose tissue: implications for cell-based therapies," Tissue Eng., vol. 7, pp. 211-228 (2001).

\* cited by examiner

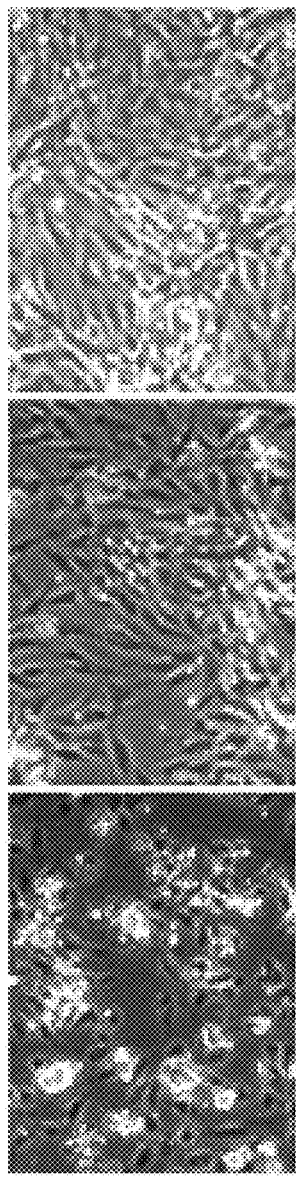
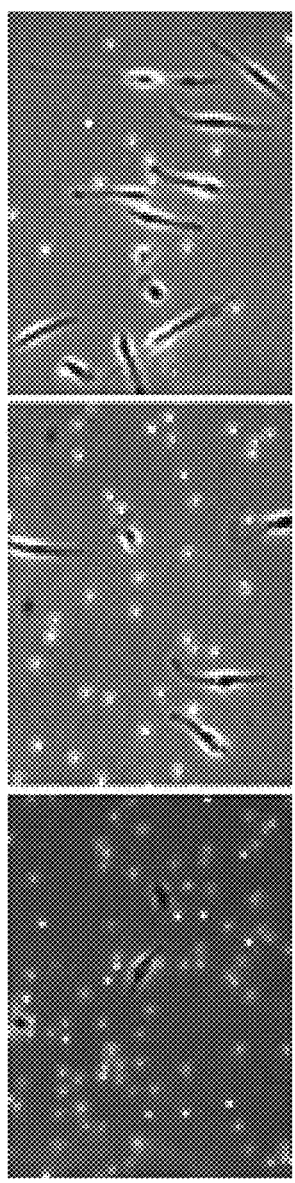
Fig. 1A
Fig. 1B

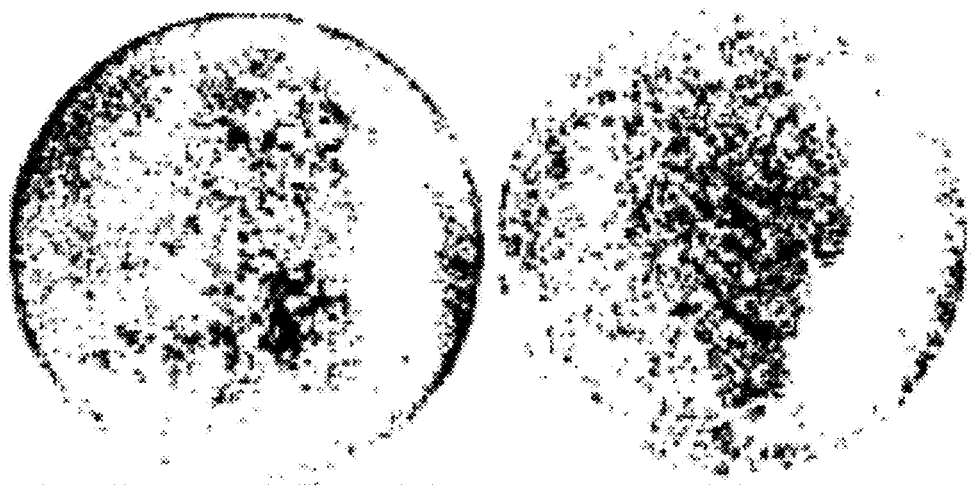
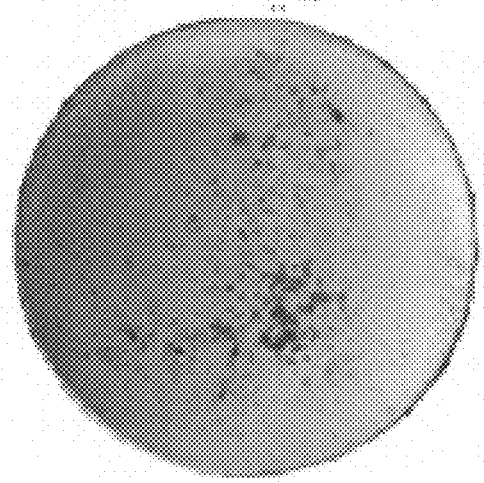
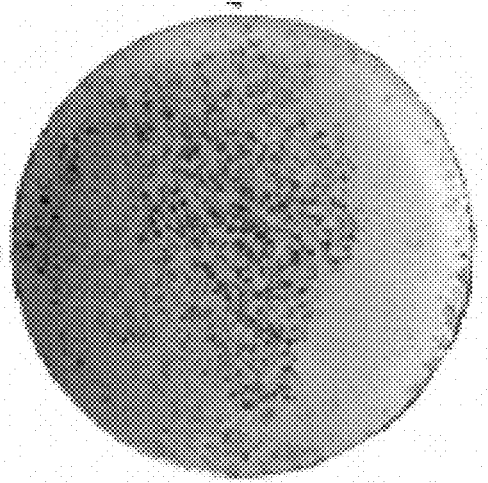
Fig. 3A  Fig. 3B  Fig. 3C  Fig. 3D

NON-ENZYMATIC METHOD FOR ISOLATING HUMAN ADIPOSE-DERIVED STROMAL STEM CELLS

This application claims priority under 35 U.S.C. §119(e) from U.S. Provisional Application Ser. No. 61/570,495, filed 14 Dec. 2011, entitled "A Non-Enzymatic Method for Isolating Human Adipose-Derived Stromal Stem Cells," the contents of which are fully incorporated by reference herein.

This invention involves a simple wash method to separate adipose-derived stromal stem cells from adipose tissue, and culturing such cells for future use, for example, for tissue regeneration. This simple method does not use enzymes to disassociate the adipose tissue, and the cells produced by the simple wash method display a different immunophenotype than cells produced using the enzyme collagenase.

Adipose tissue is recognized as an abundant and reliable source of adult stromal stem cells for tissue engineering and regenerative medicine (1-4). Adipose tissue is composed of multiple cell types, including adult adipocytes, vascular cells, and stromal stem cells. Historically, adipose-derived stromal stem cell (ASCs) isolation has relied on adipose tissue digestion with a collagenase enzyme of bacterial origin (5-7; 19-20). The quality and consistency of collagenase products between lots and vendors has been a recurring issue in producing ASCs with consistent properties (8). Additionally, the digestion of adipose tissue with collagenase has been considered to be more than "minimally manipulated," as defined by Food and Drug Administration guidance documents as "processing that does not alter the original relevant biological characteristics of cells" (9). Clinical grade collagenase is expensive and adds substantially to the cost of a final adipose stromal stem cell product for patient use. Currently, enzymatic digestion provides the basis for closed system devices approved for use in Asia and Europe for the isolation of autologous stromal vascular fraction (SVF) cells at the point of care (10). The SVF cells often refer to cell populations isolated from adipose tissue that are not adipocytes.

To reduce complexities such as cost, time, and heterogeneity of isolating stromal stem cells from adipose tissue, alternative means of isolating ASCs have been tried. ASCs within distinct and autologous donor adipose tissues are highly heterogeneous due to the type of isolation method utilized (11). A method was developed to wash the adherent ASCs one hour after plating cells that were digested with collagenase (11). This simple step of washing the plated ASCs not only significantly reduced the extraneous mesenchymal stem cells, endothelial cells, smooth muscle cells, and pericytes, but also increased the presence of stem cell markers nestin, oct4, and sall1 (11). Rat ASCs that were isolated using the standard method of an enzymatic digestion were compared with rat ASCs isolated by antibodies using immunomagnetic beads (12). Despite the lower yields, rat ASCs isolated using antibodies had a greater capacity for osteogenic differentiation and a higher expression of stem cell markers CD44, CD90, and Stro-1, than the rat ASCs isolated using the enzymatic method (12).

Another approach using non-enzymatic means of isolating ASCs from human lipoaspirates has been reported (13). The quantity and quality of adherent ASCs obtained from the bloody infranatant fraction of a human subcutaneous lipoaspirate, termed "liposuction aspirate fluid (LAF)" cells, was compared to ASCs obtained by collagenase digestion of the supernatant or floating adipose tissue, termed "processed lipoaspirate (PLA)" cells (13). After one week in culture, approximately 3-fold greater ASCs were obtained from PLA cells ($9.7 \times 10^7$) relative to LAF cells ($3.0 \times 10^7$) (13). Both ASC populations showed similar doubling times, and similar adipogenic and osteogenic differentiation capacity (13). While the freshly isolated LAF cells differed in expression of CD29, CD34, CD45, and CD90 relative to PLA cells, the surface immunophenotype of the two populations was comparable after adherence and after a 1 to 2 week culture expansion (13). LAF cells were found to have clinical utility similar to that of PLA cells (13).

International Publication No. WO 01/62901 describes the isolation of adipose tissue derived stromal cells using collagenase, and induction of such isolated cells into hematopoietic, neuronal, astroglial, hepatic or other cell lineages.

U.S. Pat. Nos. 6,777,231 and 7,470,537 describe dissociation of the adipose tissue using collagenase to isolate the lipo-derived stem cells from the lipid lattice, and differentiation of the collagenase-isolated stem cells into several tissue cell types.

U.S. Pat. Nos. 7,390,484; 8,119,121; and 8,226,947 describe methods of treatment using autologous adipose tissue implants with a concentrated population of adipose-derived stem cells, and a sterile contained method to produce the adipose-derived stem cell population.

U.S. Pat. No. 8,119,398 describes adipose-derived stem cells isolated using collagenase for tissue regeneration and wound healing.

We have developed a simple method of isolating ASCs from the floating adipose tissue of human lipoaspirate through a washing process that does not require the use of enzymes, antibodies, filters, or mechanical disruption beyond shaking the cells. The resulting ASCs isolated by the simple wash method have lower levels of CD34 expression, a hematopoietic stem cell marker, as compared to ASCs isolated using conventional enzymatic digestion using collagenase. This characteristic is consistent with non-enzymatically treated stem cells obtained from bone marrow aspirates, which are negative for CD34. Additionally, the washed ASCs have higher levels of CD44 expression, a hyaluronate receptor, and lower levels of contaminating hematopoietic cells, as evidenced by low CD45 expression, as compared to enzymatically digested cells. This difference in surface receptors may have consequences with respect to the probability of tissue rejection with allogeneic transplantation. The cells produced by this simple method can be used therapeutically for allogenic or autologous tissue regeneration, and can be administered using any pharmaceutically acceptable carrier. In addition, the cells can be administered in a matrix, lattice, scaffold, or other biologically compatible materials.

BRIEF DESCRIPTION OF DRAWINGS

FIG. 1A illustrates images of proliferating ASCs isolated enzymatically (Collagenase ASCs) from the floating adipose tissue of a lipoaspirate from a single donor taken from T-175 flasks on Days 1, 3 and 4 (magnification 10×).

FIG. 1B illustrates images of proliferating ASCs isolated non-enzymatically from the floating adipose tissue of a lipoaspirate (Wash ASCs) from a single donor taken from T-175 flasks on Days 1, 2, 3, 5, 6, and 7 (magnification 10×).

FIGS. 3A-3D illustrate the comparable adipogenic differentiation in 1 well of a 12-well plate (surface area=3.8 cm$^2$ or 12778 pixels) using either Collagenase ASCs or Wash ASCs from the same donor specimen. FIG. 3A represents an image of Collagenase ASCs cultured for adipogenesis and stained with Oil Red O. FIG. 3B represents Collagenase ASCs from FIG. 3A with threshold pixel quantification of the Oil Red O staining using ImageJ software. FIG. 3C represents an image of Wash ASCs cultured for adipogenesis and stained with Oil Red O. FIG. 3D represents Wash ASCs from FIG. 3C with threshold pixel quantification of the Oil Red O staining using ImageJ software.

FIG. 4A represents an image of Collagenase ASCs cultured for osteogenesis and stained with Alizarin Red. FIG. 4B represents Collagenase ASCs from FIG. 4A with threshold pixel quantification of the Alizarin Rec staining using ImageJ software. FIG. 4C represents an image of Wash ASCs cultured for osteogenesis and stained with Alizarin Red. FIG. 4D represents Wash ASCs from FIG. 4C with threshold pixel quantification of the Alizarin Red staining using ImageJ software.

DETAILED DESCRIPTION

Definitions

Figure 2:
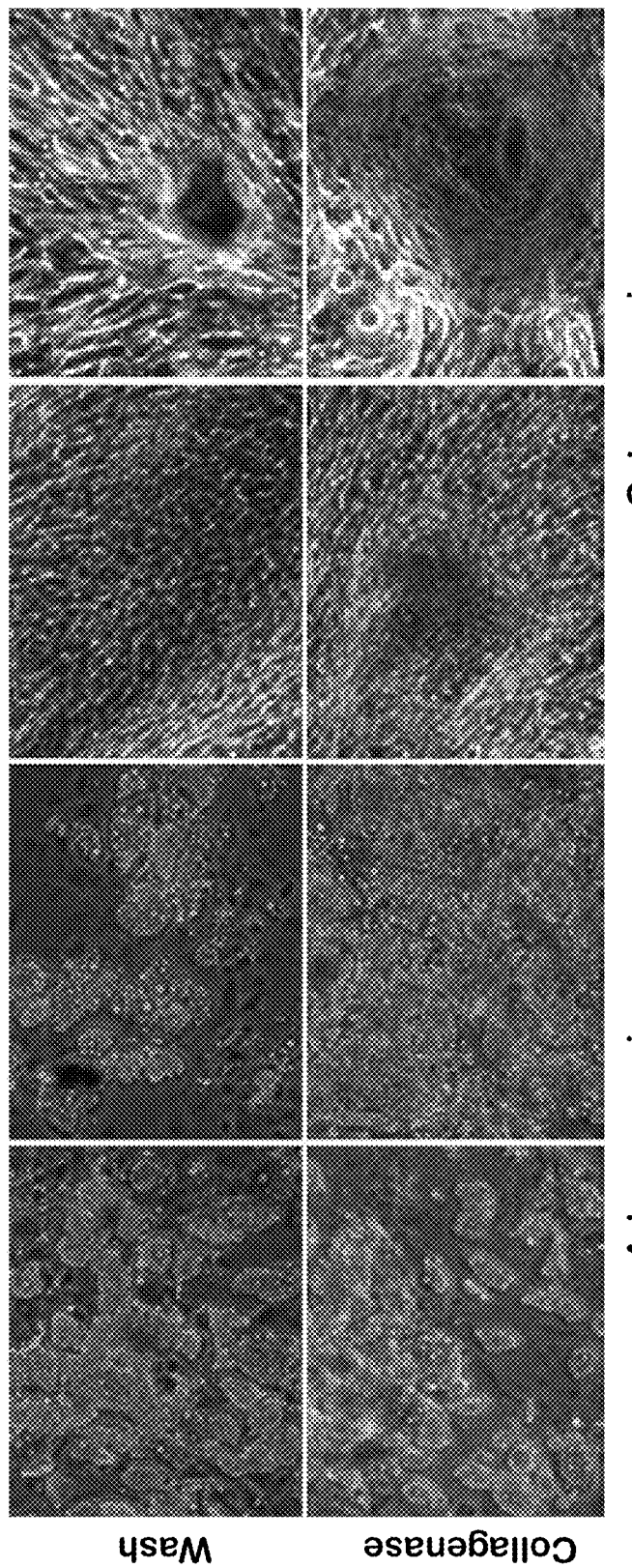
FIG. 2 illustrates images of the adipogenic and osteogenic differentiation of the enzymatic (Collagenase) and non-enzymatic (Wash) ASCs from three representative donors (magnification 10×).

"Adipose tissue" as used herein and in the claims is defined as a tissue containing multiple cell types, including adipocytes, vascular cells, preadipocytes and/or stromal stem cells. Adipose tissue is found throughout the body, but concentrated at sites including, but not limited to, the subcutaneous dermal layer, the abdominal cavity or viscera, retroperitoneal, bone marrow, and surrounding vital organs such as the heart and kidney.

"Lipoaspirate" as used herein and in the claims is defined as adipose tissue removed from the body through the use of tumescent liposuction, or adipose tissue that has been removed surgically, chopped/minced and mixed with buffer. During liposuction, the surgeon commonly introduces a buffered saline solution into the subcutaneous adipose tissue layer of a patient, subsequently removes both adipose tissue and buffered saline solution by the use of a suction pump apparatus, and collecting the fluid/tissue suspension into a closed container. This suspension will settle, with or without the use of centrifugation, into a "supernatant" or upper floating adipose layer containing the remaining intact adipose tissue fragments and any free lipid released from disrupted or lysed adipocytes and an "infranatant" or lower liquid buffered saline solution containing red blood cells and a mixed population of released cells and cellular debris.

"Stromal Vascular Fraction (SVF) Cells" as used herein and in the claims is defined a heterogeneous cell population isolated from adipose tissue after most of the mature adipocytes, erythrocytes, and debris have been removed. The SVF can come from mechanically minced adipose tissue resected surgically from the body or from lipoaspirate, and are the result of separation of the mature adipocytes from other types of cells. The SVF cells can be isolated using the two methods described below in Example 1. One common method is the use of tissue digestion of the supernatant of the lipoaspirate, using enzymes including but not limited to collagenase type I, dispase, hyaluronidase, and/or DNase. Our new isolation method washes the lipoaspirate supernatant several times with buffer, and collects the wash to isolate the SVF cells. SVF is characterized by the presence of multiple cell types which can include, depending on the isolation technique, endothelial cells, fibroblasts, lymphoid lineage cells, myeloid lineage cells, erythrocytes, pericytes, pre-adipocytes, and stromal stem cells. The SVF cells can be delineated by the use of flow cytometry for detection of surface antigens with specific monoclonal antibodies. As defined in this document, SVF cells have not been further cultured by exposing to an adherent biomaterial or plasticware, but have remained in suspension prior to use. In addition, SVF cells as indicated below can be isolated using collagenase, and are then termed "Collagenase SVFs". If the SVF cells are isolated using only the wash method described below, then they are termed "Wash SVFs." The Wash SVFs are distinct from the Collagenase SVFs based on their surface immunophenotype as outlined in Table 5.

"Adipose derived stromal stem cells (ASCs)" as used herein and in the claims are defined as the multipotent, adherent subpopulation enriched from the SVF cells by adherence to a plastic surface and culturing in a supportive stem cell culture medium. The ASCs are characterized by their ability to differentiate along one or more of the following lineage pathways: adipocyte, chondrocyte, endothelial, or osteoblast. Furthermore, the ASC can be delineated by the use of flow cytometry for the detection of characteristic surface antigens, including but not limited to, the positive expression of CD29, CD34, CD44, CD73, CD90, CD105, and the negative expression of CD11, CD14, and CD45. As defined in this document, "Collagenase ASCs" are cells that have been cultured from the Collagenase SVFs which were isolated from adipose tissue by enzymatic digestion, plastic adherence, and culture expansion. In contrast, "Wash ASCs" are cells that have been cultured from the Wash SVFs which were isolated from the lipoaspirate supernatant using only washing with buffer. The Wash ASCs are distinct from the Collagenase ASCs based on their surface immunophenotype as outlined in Table 6.

We developed a simple method of isolating ASCs from the floating adipose tissue of human lipoaspirate using only a washing process. Our simple method does not require the use of enzymes, antibodies, filters, or mechanical disruption beyond shaking the cells. The Wash ASCs were shown to be pluripotent and to have, at a minimum, a capacity for both adipogenic and osteogenic differentiation. The resulting ASCs isolated by the simple wash method were shown to have lower levels of CD34 expression, a hematopoietic stem cell marker, when compared to isolated using collagenase. Additionally, the Wash ASCs have higher levels of CD44 expression, a hyaluronate receptor, and lower levels of contaminating hematopoietic cells, as evidenced by low CD45 expression, as compared to enzymatically digested cells. This difference in surface receptors may have consequences with respect to the probability of tissue rejection with allogeneic transplantation. The cells produced by this simple method can be used therapeutically for allogenic or autologous tissue regeneration, and can be administered using any pharmaceutically acceptable carrier. In addition, the cells can be administered in a matrix, lattice, scaffold, or other biologically compatible materials, including with body tissue.

The preferred method of isolating ASCs is to extract adipose tissue from a mammalian donor either surgically or by lipoaspiration. If extracted surgically, the tissue will need to be chopped into smaller pieces and rinsed with a saline buffer. The saline/tissue mixture is then allowed to settle, and the floating adipose tissue is separated from the lower aqueous aspirate fluid which contains debris and other materials. The floating adipose tissue is mixed with buffer maintaining a temperature between about 25° C. and about 45° C., and the mixture is vigorously shaken by hand until the mixture is homogeneous. The time of shaking is preferably less than 5 min, and more preferably equal to or less than 2 min. The mixture is then allowed to settle out into two phases—an upper supernatant and a lower infranatant. The upper supernatant contains primarily adipocytes or clusters of adipocytes, while the lower infranatant contains loose cells of the stromal vascular fraction, including cells that can be cultured into adipose-derived stromal stem cells. The upper supernatant is mixed once again with buffer, and the mixing and settling process repeated. The lower infranatants from the mixing are combined, and the mixture is centrifuged so that the cells settle to the bottom as a cell pellet. The cells in this cell pellet are resuspended in stromal medium, and at this point are the SVF cells. The SVF cells are used to plate and culture the cells as adipose-derived stromal stem cells. Importantly, this method does not digest the adipose tissue with any enzyme, including the enzyme collagenase. The method does not use antibodies or filters to separate the stem cells, nor any mechanical device for disruption of the adipose tissue.

The cultured adipose-derived stromal stem cells produced without using enzymatic digestion by the wash method described above were shown to have a different immunophenotype than cells produced using collagenase. These cells had a CD marker profile of lower levels of CD45 and CD34 and higher levels of CD44, CD73, and CD90 as compared to levels from human adipose-derived stromal stem cells produced using enzymatic digestion.

These adipose-derived stromal stem cells (Wash ASCs) with the unique CD marker profile can be used for tissue differentiation into one or more tissues selected from the group consisting of adipose tissue, bone tissue, cartilage tissue, vascular tissue, skeletal muscle tissue, and skin tissue. These Wash ASCs can be used in combination with other biologically compatible materials to promote tissue regeneration both in vivo and in vitro.

In addition, the stromal vascular fraction cells collected using the wash method (Wash SVFs; the cells in suspension prior to culturing) can be used for tissue differentiation into one or more tissues selected from the group consisting of adipose tissue, bone tissue, cartilage tissue, vascular tissue, skeletal muscle tissue, and skin tissue. These Wash SVFs can be used in combination with other biologically compatible materials to promote tissue regeneration both in vivo and in vitro.

Example 1

Material & Methods

Donor Demographics:

The source of adipose tissue was the subcutaneous lipoaspirates collected from 12 females and one male. The 13 participants were profiled based on age, BMI, and serum biomarker characteristics using standard techniques and the results shown in Table 1. When compared to 21 other random lipoaspirate donors as controls (Age: 43.0±10.7; BMI: 25.4±3.3; HOMA-IR: 0.8±1.2; p>0.05), it can be seen that the 13 participants for this study are representative of the larger donor pool.

TABLE 1

Donor Demographics & Serum Analysis Data

| Donor Number | Study Subjects n = 13 | Controls n = 21 | Statistical Significance |
|---|---|---|---|
| Donor Age (years) | 44.3 ± 11.3 | 43.0 ± 10.7 | p = 0.85 |
| BMI (kg/m$^2$) | 26.43 ± 4.2 | 25.4 ± 3.3 | p = 0.34 |
| Glucose (mg/dL) | 81.2 ± 16.9 | 76.9 ± 18.0 | p = 0.53 |
| Cholesterol (mg/dL) | 182.1 ± 39.0 | 184.3 ± 30.2 | p = 0.88 |
| HDL (mg/dL) | 55.3 ± 16.3 | 62.5 ± 10.9 | p = 0.25 |
| LDL (mg/dL) | 107.9 ± 32.3 | 104.3 ± 25.9 | p = 0.77 |
| HOMA-IR | 0.8 ± 0.7 | 0.8 ± 1.2 | p = 0.98 |
| Insulin (µLU/mL) | 3.9 ± 3.3 | 3.7 ± 4.3 | p = 0.89 |
| Triglyceride (mg/dL) | 94.3 ± 33.0 | 87.7 ± 47.6 | p = 0.66 |

Tissue Processing:

The lipoaspirate from adipose tissue was stored at room temperature and processed within the first 24 hours of receiving the lipoaspirate according to published methods (14, 15).

Isolating hASCs Using an Enzymatic Digestion (Method 1):

Between 11 and 100 mL of lipoaspirate was poured into a 250 mL bottle with an equal volume of pre-warmed phosphate-buffered solution (PBS). The bottle was then shaken thoroughly to wash the tissue, and then allowed to separate based on density into a floating adipose tissue supernatant and an aqueous aspirate fluid infranatant. The aspirate fluid and PBS infranatant was discarded. The floating adipose tissue was further washed with PBS 2 to 3 times to remove the majority of the remaining erythrocytes. A collagenase solution was prepared [0.1% Collagenase Type I CLS 270 u/mg (Worthington Biochemical Corporation, Lakewood, N.J.), 1% Albumin (Sigma-Aldrich, St. Louis, Mo.), PBS, and 2 mM $CaCl_2$], sterile-filtered and warmed in a 37° C. water bath. The washed floating adipose tissue was suspended in an equal volume of collagenase solution and digested in a sealed 250 mL container, and rocked at 37° C. for 60 minutes in a hybridization oven (Boekel Industries, Inc., Feasterville-Trevose, Pa.). The container was then centrifuged twice at 1,200 rpm for 5 min at room temperature. The topmost layers of oil, fat, and collagenase solution in the bottle were removed and discarded, leaving behind the undisturbed stromal vascular fraction (SVF) pellet. The cells in this pellet are the Collagenase SVF cells. This pellet was resuspended in stromal medium [Dulbecco's modified Eagle medium (DMEM)/Hams F-12 medium supplemented with 10% Fetal Bovine Serum (Hyclone, Logan, Utah) and a 1% prepared antibiotic/antimycotic solution (Penicillin 100 units/mL; streptomycin 100 µg/mL; amphotericin 250 ng/mL; MP Biomedicals, Solon, Ohio)]; and the cells plated into T-175 tissue culture flasks (0.2 mL medium/cm2) (Fisher Scientific, Dallas, Tex.) (35 mL of tissue per 175 cm$^2$ surface area). The cells after being plated and cultured are the Collagenase ASCs. The flasks were then kept humidified in an incubator at 37° C. and with 5% CO2.

Isolating hASCs Using a Non-Enzymatic Digestion (Method 2):

Between 60 and 200 mL of floating adipose tissue from the lipoaspirate was poured into 250 mL containers with no more than 50 mL of PBS. The bottles were vigorously shaken by hand for approximately 1-2 minutes until bubble cavitation occurred in the suspension, and the suspension reaches a homogeneous appearance both in color and texture. After shaking, the suspension was allowed to settle into a fatty supernatant containing intact adipose tissue fragments and an aqueous infranatant containing isolated individual cells or cell clumps. The aqueous infranatant was saved in 50 mL conical tubes. The fatty supernatant was washed another 2-3 times, each time saving the aqueous infranatant. The conical tubes with the infranatants were centrifuged at 1,200 rpm for 5 min at room temperature. The cell pellet from centrifugation contained the Wash SVF cells. These Wash SVF cells were resuspended in stromal medium (as described above) and then plated into T-175 flasks (35 mL of tissue per 175 cm$^2$ surface area). The plated and cultured cells are the Wash ASCs. The flasks were maintained in a humidified incubator at 37° C. and with 5% CO2.

Stromal Vascular Fraction Analysis:

Fluorescence-activated cell sorting (FACS) was performed on four female donors on both Collagenase and Wash SVFs obtained from Methods 1 and 2 as above. Each SVF population was first filtered with a 40 µm nylon cell strainer (BD Falcon, Franklin Lakes, N.J.), and then mixed with 10 mL of red blood cell lysis buffer for 5 min at room temperature. To halt the lysis, the cells were resuspended with 20 mL of PBS. The cells were centrifuged for 5 min at 1200 rpm at room temperature and resuspended in approximately 500 uL of cold PBS. These cells were then distributed in 50 µL aliquots in 10×1.5 mL microcentrifuge tubes. Next, 5-10 µL of fluorochrome-conjugated monoclonal antibodies were added to the cells. The samples were left to incubate in the dark for 1 h at room temperature, and then washed with 1 mL 1% BSA in cold PBS three times. Last, the samples were resuspended in 500 µL of 1% formaldehyde in PBS for fixation. Samples were acquired on a FACS Calibur flow cytometer (BD Biosciences, San Jose, Calif.) utilizing a 15 mW 488 nm argon-ion laser and configured for Fluorescein and Phycoerythrin fluorescence measurements using log amplification. Between 2,000-9,000 cells per sample were acquired on a Macintosh G5 workstation (Apple Computer, Cupertino, Calif.) running Cellquest Pro software (BD Biosciences, San Jose, Calif.). Cell debris was eliminated by gating on intact cells based on dot plots of forward scatter versus side scatter. Fluorescence analyses in the form of histograms were illustrated (data not shown) using Cellquest Pro software (BD Biosciences, San Jose, Calif.). Percentages of cells expressing CD29 (eBioscience catalog number 12-0297, San Diego, Calif.), CD105 (eBioscience catalog number 12-1057), CD45 (eBioscience catalog number 12-0459), CD34 (BD Biosciences catalog number 348057), CD44 (BD Biosciences catalog number 347943), CD73 (BD Pharmingen catalog number 550257, San Diego, Calif.), and CD90 (BD Pharmingen catalog number 55596) were determined for each sample based on comparisons with isotype matched controls, PE IgG1 (BD Biosciences catalog number 555749) and FITC IgG1 (BD Biosciences catalog number 554679). These markers are shown in Table 2.

TABLE 2

Antigen Marker Reference Table

| | |
|---|---|
| CD29 | Integrin Beta-1 |
| CD105 | Endoglin |
| CD45 | Leukocyte Common Antigen |
| CD34 | Hematopoietic Stem Cell Marker, Sialomucin |
| CD44 | Hyaluronic Acid Receptor |
| CD73 | 5' Ecto Nucleotidase |
| CD90 | Thy 1 |
| CD31 | PECAM-1 (Platelet Endothelial Cell Adhesion Molecule) |
| CD14 | Endotoxin Receptor |
| CD15 | Lewis X |
| CD146 | Muc-18, Pericyte Marker |

Expansion:

After 24 h of plating, the adherent Collagenase ASCs or Wash ASCs were washed with PBS and fed with stromal medium. Every 2-3 days, the medium was changed in the flasks, until the cells reached 80-90% confluency. At confluency, the cells were analyzed by FACS as described above and passaged for differentiation.

Flow Cytometry:

At passage 0, between 1 and 1.5 million ASCs (either Collagenase ASCs or Wash ASCs) were washed twice with cold PBS and resuspended in approximately 500 µL cold PBS. The same protocol used to stain the stromal vascular fraction as described above was used to analyze 10,000 cells per sample. As with the stromal vascular fractions, percentages of cells expressing CD29, CD105, CD45, CD34, CD44, CD73, and CD90 were determined for each sample based on comparisons with isotype matched controls, PE IgG1 and FITC IgG1.

Differentiation:

At passage 1 or 2, either Collagenase ASCs or Wash ASCs were plated into 12-well plates (Fisher Scientific, Dallas, Tex.) at a density of 10,000-25,000 cells/cm$^2$. The cells were induced for either adipogenic or osteogenic differentiation lineage using the appropriate medium, with the stromal wells left as controls. The adipogenic medium included DMEM High Glucose/F-12 (Hyclone, Logan, Utah), 3% FBS, 1% antibiotic/antimycotic (described above), 33 µM Biotin, 17 µM pantothenate, 100 nM insulin, 1 µM dexamethasone, 500 µM isobutylmethylxanthine, and 5 µM rosiglitazone (AK Scientific, Mountain View, Calif.). The osteogenic medium included DMEM F-12, 10% FBS, 1% B-Glycerophosphate (1M), 0.1% Ascorbate (50 mg/mL), and 0.01% dexamethasone (1 mM). The cells were then maintained for 10-14 days. At this point the wells were stained for evidence of alizarin red (osteogenic wells) or Oil red O (adipogenic wells).

Example 2

Tissue Processing: Time, Culture, and Yield

The total tissue processing time up to the plating of the Collagenase SVFs to obtain Collagenase ASCs took approximately 3 hours or longer. Total processing time up to plating of the Wash SVFs to become Wash ASCs took only about 1 hour.

The Collagenase ASCs were cultured in T-175 tissue culture flasks (~35 mL of lipoaspirate digest per flask) for 3-13 days (average of about 6 days). Representative images of the Collagenase ASCs are shown in FIG. 1A, for days 1, 3 and 4. At 80-90% confluency, the cells were harvested, giving an average yield of about 20 million cells, or about 480,000 cells per milliliter of lipoaspirate. This yield is consistent with previously published results using an enzymatic digestion (15, 17).

The Wash ASCs were similarly cultured in T-175 flasks for 7-21 days (average of about 13 days). Representative images of the Wash ASCs are shown in FIG. 1B, for days 1, 2, 3, 5, 6 and 7. The average Wash ASC yield for this method was about 3 million cells, or about 25,000 cells per milliliter of lipoaspirate. After culturing, the Collagenase ASC yield was about 19-fold higher than the yield from the Wash ASCs in terms of cells per milliliter of tissue used.

Example 3

Differentiation Potential of ASCs

After 10-14 days of culture, the Collagenase ASCs and the Wash ASCs showed comparable differentiation potential, for example, in the potential for adipogenesis and osteogenesis. The cells were cultured in the appropriate differentiation media as described in Example 1, and then stained appropriately using Oil Red O stain for adipogenic cells and Alizarin Red stain for osteogenic cells. FIG. 2A shows representative images of both Wash ASCs and Collagenase ASCs cultured in adipogenesis medium and then stained with Oil Red O. FIG. 2A shows representative images of Wash ASCs or Collagenase ASCs cultured in the osteogenesis medium and stained with Alizarin Red. The ASCs that differentiated into osteocytes formed calcium deposits as shown by the Alizarin red staining.

To determine the percentage of Oil red O and Alizarin red stain uptake in each of the wells, the color deconvolution plug-in on the ImageJ software version 1.44 was used. This determination quantified the differentiation potential for ASCs from each donor isolated using both the collagenase and the wash methods. FIGS. 3A-3D illustrate the comparable adipogenic differentiation in 1 well of a 12-well plate (surface area=3.8 cm2 or 12778 pixels) using Wash ASCs and Collagenase ASCs from the same donor specimen. FIG. 3A represents an image of Collagenase ASCs cultured for adipogenesis and stained with Oil Red O. FIG. 3B represents Collagenase ASCs from FIG. 3A with threshold pixel quantification of the Oil Red O staining using ImageJ software. FIG. 3C represents an image of Wash ASCs cultured for adipogenesis and stained with Oil Red O. FIG. 3D represents Wash ASCs with threshold pixel quantification of the Oil Red O staining using ImageJ software.

Figure 4A:
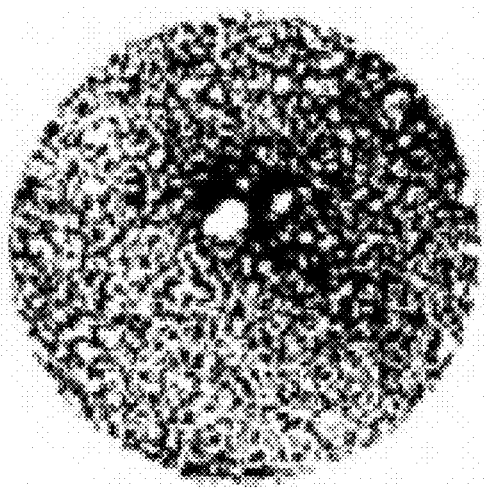
FIGS. 4A-4D illustrate the comparable osteogenic differentiation in 1 well of a 12-well plate (surface area=3.8 cm$^2$ or 12778 pixels) using either Collagenase ASCs or Wash ASCs from the same donor specimen.
Figure 4B:
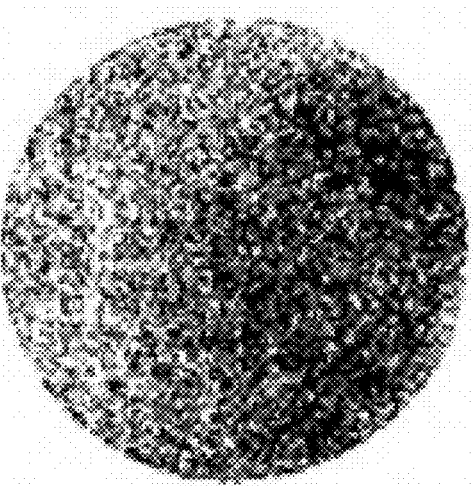
Figure 4C:
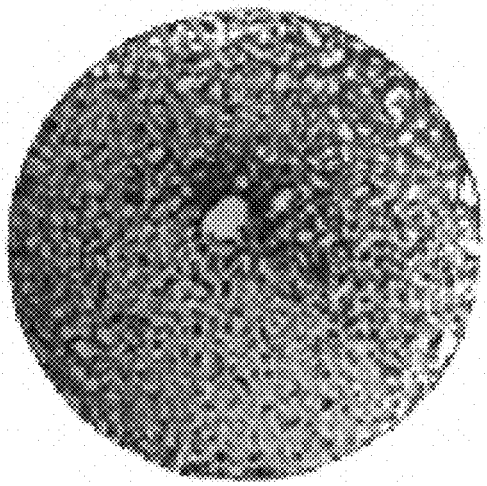
Figure 4D:
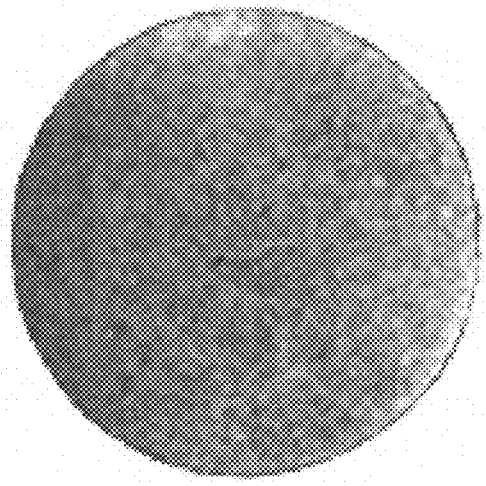

Similarly, FIGS. 4A-4D illustrate the comparable osteogenic differentiation in 1 well of a 12-well plate (surface area=3.8 cm2 or 12778 pixels) using either Collagenase ASCs or Wash ASCs from the same donor specimen. FIG. 4A represents an image of Collagenase ASCs cultured for osteogenesis and stained with Alizarin Red. FIG. 4B represents Collagenase ASCs from FIG. 4A with threshold pixel quantification of the Alizarin Rec staining using ImageJ software. FIG. 4C represents an image of Wash ASCs cultured for osteogenesis and stained with Alizarin Red. FIG. 4D represents Wash ASCs from FIG. 4C with threshold pixel quantification of the Alizarin Red staining using ImageJ software.

Using the ImageJ software, the average percentage of Collagenase ASCs showing adipogenic differentiation was 14.7%, while the average percentage of Wash ASCS showing adipogenic differentiation was 13.6% (p=0.8). The average percentage of Collagenase ASCs showing osteogenic differentiation was 64.5%, while the average percentage of Wash ASCS showing osteogenic differentiation was 65.6% (p=0.89). As shown by Tables 3 and 4, the percentage of adipogenic and osteogenic differentiation of Collagenase ASCs is not significantly different from using Wash ASCs.

TABLE 3

Collagenase ASCs vs. Wash ASCs Adipogenic Differentiation

| Donor | Collagenase ASCs % Differentiation (Area = 3.8 cm$^2$) (n = 5) | Wash ASCs % Differentiation Area = 3.8 cm$^2$) (n = 8) |
|---|---|---|
| 1 | — | 22.6 |
| 2 | 13.3 | 2.6 |
| 3 | 18.6 | 21.5 |
| 4 | — | 21.2 |
| 5 | — | 7.4 |
| 6 | 7.0 | 9.8 |
| 7 | 25.9 | 7.5 |
| 8 | 8.9 | 16.4 |
| Average | 14.7 ± 7.7 | 13.6 ± 7.7 |
| T-Test | p = 0.8, no significance (where p < 0.05 is significant) | |

TABLE 4

Collagenase ASCs vs. Wash ASCs Osteogenic Differentiation

| Donor | Collagenase ASCs % Differentiation (Area = 3.8 cm$^2$) (n = 4) | Wash ASCs % Differentiation (Area = 3.8 cm$^2$) (n = 6) |
|---|---|---|
| 1 | 65.6 | 65.6 |
| 2 | — | 45.7 |
| 3 | — | 60.3 |
| 4 | 67.3 | 86.3 |
| 5 | 54.1 | 60.5 |
| 6 | 70.9 | 74.3 |
| Average | 64.5 ± 7.3 | 65.5 ± 13.8 |
| T-Test | p = 0.89, no significance (where p < 0.05 is significant) | |

Example 4

Immunophenotype of ASCs

The immunophenotype of the Collagenase ASCs and Wash ASCs was analyzed based using a cluster of differentiation markers that are characteristic of human ASCs. Flow cytometry was used to test for this panel of markers on the Collagenase SVF and the Wash SVF as well as passage 0 cells. The results are shown as a percentage in Tables 5 and 6.

TABLE 5

Flow Cytometry Data - Stromal vascular fraction (SVF)

| Antigen | Collagenase SVF (n = 4) | Wash SVF (n = 4) | Statistical Significance[a] |
|---|---|---|---|
| huCD29 | 90.1 ± 8.1 | 48.3 ± 32.0 | NS |
| huCD105 | 37.4 ± 20.0 | 3.9 ± 5.5 | * |
| huCD45 | 27.7 ± 14.5 | 81.7 ± 15.6 | ** |
| huCD34 | 81.2 ± 14.7 | 23.7 ± 21.2 | * |
| huCD44 | 6.3 ± 3.1 | 4.8 ± 2.9 | NS |
| huCD73 | 37.2 ± 17.5 | 8.8 ± 6.4 | * |
| huCD90 | 80.9 ± 10.1 | 23.2 ± 24.5 | * |
| PE IgG1 | 0.9 ± 0.9 | 0.9 ± 1.1 | NS |
| FITC IgG1 | 1.2 ± 0.6 | 1.4 ± 1.5 | NS |
| Control | 0.5 ± 0.2 | 1.0 ± 1.7 | NS |

[a]Where * signifies p < 0.05, ** signifies p < 0.005, and NS is not significant.

TABLE 6

Flow Cytometry Data - Passage 0 ASCs

| Antigen | Collagenase ASCs (n = 8) | Wash ASCs (n = 12) | Statistical Significance[a] |
|---|---|---|---|
| huCD29 | 97.8 ± 3.2 | 99.3 ± 1.0 | NS |
| huCD105 | 97.0 ± 3.5 | 99.8 ± 0.1 | NS |
| huCD45 | 6.4 ± 3.6 | 1.7 ± 1.4 | ** |
| huCD34 | 65.3 ± 36.3 | 10.7 ± 9.2 | *** |
| huCD44 | 12.7 ± 6.0 | 44.8 ± 11.0 | *** |
| huCD73 | 89.2 ± 6.4 | 99.7 ± 0.3 | ** |
| huCD90 | 94.1 ± 3.4 | 99.7 ± 0.3 | ** |
| PE IgG1 | 3.9 ± 2.5 | 1.6 ± 1.5 | * |
| FITC IgG1 | 4.3 ± 2.8 | 1.9 ± 1.7 | NS |
| Control | 3.7 ± 2.4 | 1.1 ± 1.1 | * |

[a]Where * signifies $p < 0.05$,  signifies $p < 0.005$, * signifies $p < 0.001$, and NS is not significant.

For the stromal vascular fractions, Table 5 shows that the percentages are variable in the markers expressed. The Wash SVF has an increased population of hematopoetic cells, as seen with an increased expression of CD45, compared to the Collagenase SVF.

For the passage 0 Wash ASCs, CD29 and CD105 did not show any difference from the Collagenase ASCs (Table 6; p=0.25 and p=0.05 respectively). However, the markers CD45, CD34, CD44, CD73, and CD90 showed a significant difference between the Collagenase ASCs and the Wash ASCs (p<0.05). The Wash ASCs expressed a lower positive for CD45, CD34, as well as the isotype control antibodies; and a higher positive for CD44, CD73, and CD90, as compared to the Collagenase ASCs. Collagenase can change the phenotype of ASCs since collagenase digests the triple helix region of peptide bonds in the collagen of adipose tissue. The Wash ASCs displayed a distinct and potentially favorable immunophenotype, based on the above FACS analysis. The difference between the Collagenase ASCs and the Wash ASCs may reflect the chemical alteration of the cells by collagenase digestion.

Consistent with prior publications, the analysis of passage 0 ASCs shows that cells in culture overtime will express different levels of the markers (16, 17). An experiment was also done with three separate donors to determine if immunophenotype of passage 0 ASCs changes by a longer time in culture. The results are shown in Table 7. Collagenase ASCs and Wash ASCs were kept in culture for similar lengths of time (between 10-12 days) and then analyzed as above. Both types of ASCs expressed comparable levels of surface markers with couple of exceptions: both CD44 and CD90 were higher in the Wash ASCs. In addition, although not significant in this experiment, CD34 tended to be lower in the Wash ASCs. We believe that with a larger sample size, CD34 would be significantly lower in Wash ASCs.

TABLE 7

Flow Cytometry Data - Passage 0 ASCs in Culture for Similar Lengths of Time

| Antigen | Collagenase ASCs (n = 3) | Wash ASCs (n = 3) | Statistical Significance |
|---|---|---|---|
| huCD29 | 99.8 ± 0.1 | 99.8 ± 0.2 | NS; p = 0.66 |
| huCD105 | 98.5 ± 0.9 | 99.8 ± 0.1 | NS; p = 0.14 |
| huCD45 | 3.1 ± 2.7 | 2.2 ± 1.8 | NS; p = 0.68 |
| huCD34 | 23.7 ± 20.3 | 8.1 ± 1.9 | NS; p = 0.31 |
| huCD44 | 10.6 ± 8.8 | 35.6 ± 7.2 | * p = 0.02 |
| huCD73 | 92.4 ± 5.0 | 99.7 ± 0.1 | NS; p = 0.13 |
| huCD90 | 94.7 ± 0.9 | 99.4 ± 0.4 | * p = 0.01 |
| PE IgG1 | 1.4 ± 0.5 | 2.1 ± 1.9 | NS; p = 0.62 |
| FITC IgG1 | 2.1 ± 1.4 | 1.8 ± 2.3 | NS; p = 0.90 |
| Control | 1.1 ± 0.4 | 1.3 ± 1.5 | NS; p = 0.88 |

Processing lipoaspirates without collagenase by washing alone was shown to be an effective method to isolate ASCs which can reduce the cost and time required for initial isolation and tissue processing. This simple wash method of vigorously washing the floating lipoaspirate has the potential to release a substantial number of cells with adherent and differentiation potential comparable to ASCs obtained by collagenase digestion. It is noteworthy that the Wash ASCs displayed reduced levels of CD45 contamination, decreased levels of CD34, and enriched levels of the mesenchymal stromal cell markers (CD44, CD73, and CD90). Drawbacks to the washing approach are the 19-fold reduction in yield as well as the about 2.5-fold increased culture time required for the initial passage expansion relative to collagenase digestion. Nevertheless, the findings indicate that alternative, non-enzymatic methods are useful for ASC isolation, particularly when processing large volumes of lipoaspirate for autologous use.

The major difference between the Wash ASCs and the Collagenase ASCs is that the Wash ASCs have very low levels of CD34 (the hematopoietic stem cell marker/glycoprotein) with only 11% positive. In contrast, the Collagenase ASCs are 90% positive for CD34. Also, the Wash ASCs are more strongly positive for the hyaluronate receptor CD44 (48% positive) as compared to the Collagenase ASCs (14%). Finally, the level of contaminating hematopoietic cells (CD45) is lower (1-2%) in the Wash ASCs compared to the Collagenase ASCs (8%). This lowered contamination has consequences with respect to tissue rejection with transplantation allogenically.

Previous reports of washed cells isolated ASCs from the bloody infranatant fraction (the "liposuction aspirate fluid" or "LAF cells") (13), while the above Wash ASCs were taken from floating adipose tissue of the lipoaspirate (previously termed the "processed lipoaspirate" (13). Compared to the LAF cells, the ASCs from the floating adipose tissue had substantially higher levels of CD105, which was true for both the Collagenase ASCs and the Wash ASCs. In addition, the Wash ASCs had low levels of CD34, in contrast to the Collagenase ASCs from the lipoaspirate and the LAF cells from the bloody infranatant which showed high levels of CD34 (13).

Example 5

Wash ASCs Culture Expanded for Bone Repair

Human Wash ASCs will be isolated from subcutaneous lipoaspirate according to the methods described above. The adherent Wash ASCs obtained after culture expansion will be released by trypsin digestion as described using an animal protein free product [18]. The cells will be washed in warm (37° C.±5° C.) phosphate buffered saline and concentrated by centrifugation (300×g±100×g). The Wash ASCs will be resuspended in phosphate buffered saline or equivalent electrolyte balanced solution at a concentration between about $10^5$ and $10^7$ cells/mL, with an optimal concentration of about 2.5×10⁶ to about 5×10⁶ cells/mL. The resuspended cells will be loaded by capillary action and/or gravity filtration onto an osteoinductive/osteoconductive biomaterial scaffold such as but not limited to demineralized bone or hydroxyapatite tricalcium phosphate (21-22). The resulting scaffold material can then be implanted into a critical sized orthopedic or craniofacial bone defect or to an orthopedic or craniofacial bone defect at high risk of defective healing.

Example 6

Wash SVF Cells Used for Bone Repair at Point of Care

Human SVF cells will be isolated using the wash method from subcutaneous lipoaspirate according to the methods described in examples 1 & 2. The Wash SVF cells (cells prior to plating) will be loaded directly onto an osteoinductive/osteoconductive biomaterial scaffold, for example, including but not limited to, demineralized bone or hydroxyapatite tricalcium phosphate. The resulting scaffold material will then be implanted into a critical sized orthopedic or craniofacial bone defect or to an orthopedic or craniofacial bone defect at high risk of defective healing. This approach, unlike that in Example 5, will allow the immediate application of autologous derived SVF cells at point of care for the treatment of an orthopedic or craniofacial injury with a high risk of defective healing. A similar approach would be possible for other tissue defects, including but not limited to, defects of adipose tissue, vascular tissue, skeletal muscle, and skin. In each case, the Wash SVF cells from the floating adipose tissue of the lipoaspirate will be enriched by direct adherence onto an appropriate biomaterial scaffold with properties suitable for ASC adhesion and promotion of cell differentiation specific for the tissue of interest.

REFERENCES

1. Gimble J M, Katz A J, Bunnell B A. Adipose-derived stem cells for regenerative medicine. Circ Res. 2007; 100: 1249-60.
2. Gimble J M, Grayson W, Guilak F, Lopez M J, Vunjak-Novakovic G. Adipose tissue as a stem cell source for musculoskeletal regeneration. Front Biosci (Schol Ed). 2011; 3:69-81.
3. Gimble J M, Guilak F, Bunnell B A. Clinical and preclinical translation of cell-based therapies using adipose tissue-derived cells. Stem Cell Res Ther. 2010; 1:19.
4. Gimble J, Guilak F. Adipose-derived adult stem cells: isolation, characterization, and differentiation potential. Cytotherapy. 2003; 5:362-9.
5. Zuk P A, Zhu M, Ashjian P, De Ugarte D A, Huang J I, Mizuno H, et al. Human adipose tissue is a source of multipotent stem cells. Mol Biol Cell. 2002; 13:4279-95.
6. Zuk P A, Zhu M, Mizuno H, Huang J, Futrell J W, Katz A J, et al. Multilineage cells from human adipose tissue: implications for cell-based therapies. Tissue Eng. 2001; 7:211-28.
7. Rodbell M. Metabolism of Isolated Fat Cells. I. Effects of Hormones on Glucose Metabolism and Lipolysis. J Biol Chem. 1964; 239:375-80.
8. Williams S K, McKenney S, Jarrell B E. Collagenase lot selection and purification for adipose tissue digestion. Cell Transplant. 1995; 4:281-9.
9. HUMAN CELLS, TISSUES, AND CELLULAR AND TISSUE-BASED PRODUCTS. Code of Federal Regulations 2011; 21CFR1271.3(f).
10. Hicok K C, Hedrick M H. Automated isolation and processing of adipose-derived stem and regenerative cells. Methods Mol Biol. 2011; 702:87-105.
11. Griesche N, Luttmann W, Luttmann A, Stammermann T, Geiger H, Baer P C. A simple modification of the separation method reduces heterogeneity of adipose-derived stem cells. Cells Tissues Organs. 2010; 192:106-15.
12. Rada T, Gomes M E, Reis R L. A novel method for the isolation of subpopulations of rat adipose stem cells with different proliferation and osteogenic differentiation potentials. J Tissue Eng Regen Med. 2011; 5:655-64.
13. Yoshimura K, Shigeura T, Matsumoto D, Sato T, Takaki Y, Aiba-Kojima E, et al. Characterization of freshly isolated and cultured cells derived from the fatty and fluid portions of liposuction aspirates. J Cell Physiol. 2006; 208:64-76.
14. Carvalho P P, Wu X, Yu G, Dias I R, Gomes M E, Reis R L, et al. The Effect of Storage Time on Adipose-Derived Stem Cell Recovery from Human Lipoaspirates. Cells Tissues Organs. 2011.
15. Yu G WX, Dietrich M A, Polk P, Scott L K, Ptitsyn A A, Gimble J M. Yield and characterization of subcutaneous human adipose-derived stem cells by flow cytometric and adipogenic mRNA analyzes. Cytotherapy. 2010; 12:538-46.
16. McIntosh K, Zvonic S, Garrett S, Mitchell J B, Floyd Z E, Hammill L, et al. The immunogenicity of human adipose derived cells: Temporal changes in vitro. Stem Cells. 2006; 24:1245-53.
17. Mitchell J. B. MK, Zvonic S., Garrett S., Floyd Z. E., Kloster A., Halvorsen Y. D., Storms R. W., Goh B., Kilroy G. S., Wu X., Gimble. J. M. The immunophenotype of human adipose derived cells: Temporal changes in stromal- and stem cell-associated markers Stem Cells. 2006; 24:376-85.
18. Carvalho P P, Wu X, Yu G, et al. Use of animal protein-free products for passaging adherent human adipose-derived stromal/stem cells. Cytotherapy 2011 Jan. 3; 13(5):594-7
19. Jurgens W J E M, van Dijk A, Doulabi B Z, Niessen F B, Ritt M J P F, van Milligen F J, Helder M N. Freshly isolated stromal cells from the infrapatellar fat pad are suitable for a one-step surgical procedure to regenerate cartilage tissue. Cytotherapy 2009; 11(8):1052-1054.
20. Oedayrajsingh-Varma M J, van Ham S M, Knippenberg M, Helder M N, Klein-Nulend J, Schouten T E, Ritt M J P F, van Milligen F J. Adipose tissue-derived mesenchymal stem cell yield and growth characteristics are affected by the tissue-harvesting procedure. Cytotherapy 2006; 8(2):166-177.
21. Hicok K C, Du Laney T V, Zhou Y S, Halvorsen Y D, Hitt D C, Cooper L F, Gimble J M. Human adipose-derived adult stem cells produce osteoid in vivo. Tissue Eng. 2004 March-April; 10(3-4):371-80.
22. Lopez M J, McIntosh K R, Spencer N D, Borneman J N, Horswell R, Anderson P, Yu G, Gaschen L, Gimble J M. Acceleration of spinal fusion using syngeneic and allogeneic adult adipose derived stem cells in a rat model. J Orthop Res. 2009 March; 27(3):366-73.

The complete disclosures of all references cited in this specification are hereby incorporated by reference. Specifically incorporated by reference are the following: (A) F. S. Shah et al., "A Non-Enzymatic Method for Isolating Human Adipose-Derived Stromal Stem Cells," a manuscript submitted to Cytotherapy, November 2012; and (B) F. S. Shah, "A Non-Enzymatic Method for Isolating Human Adipose-Derived Stromal Stem Cells," an abstract and poster presented at the 2$^{nd}$ Midwest Conference on Stem Cell Biology and Therapy, October 5-7, 2012, Oakland University, Rochester, Mich. In the event of an otherwise irreconcilable conflict, however, the present specification shall control.

We claim:

1. A method to concentrate adipose-derived stromal stem cells from adipose tissue from a mammalian donor; said method comprising the following steps:
   (a) collecting a lipoaspirate of adipose tissue from the donor;
   (b) separating the lipoaspirate in aqueous buffer into a floating adipose layer and a lower aqueous aspirate fluid;
   (c) isolating the floating adipose layer; (d) mixing the isolated adipose layer from step (c) with buffer at a temperature between about 25° C. and about 45° C.;
   (e) shaking the mixture from step (d) for a time less than about 5 minutes, and then allowing the mixture to settle into an upper supernatant and a lower infranatant;
   (f) separating the supernatant from step (e) from the infranatant from step (e);
   (g) repeating steps (d) through (f), using in step (d) adipose cells from the separated supernatant from step (f) to mix with the buffer instead of the floating adipose layer from step (c);
   (h) combining the infranatants from all repetitions; and
   (i) centrifuging the combined infranatants into a cell pellet and a aqueous supernatant, whereby the cell pellet comprises concentrated adipose-derived stromal stem cells;

wherein the concentrated adipose-derived stromal stem cells have not been subjected to enzymatic digestion or antibody affinity purification.

2. The method of claim 1, wherein the mammalian donor is a human.

3. The method of claim 1, additionally comprising the step of resuspending the cell pellet in a medium.

4. The method of claim 3, additionally comprising the step of culturing cells from the medium suspension.

5. The method of claim 3, wherein the medium comprises stromal medium.

6. The method of claim 5, additionally comprising the step of culturing cells from the stromal medium suspension.

* * * * *